United States Patent [19]
Sakamoto

[11] Patent Number: 5,366,868
[45] Date of Patent: Nov. 22, 1994

[54] MULTILAYER ANALYTICAL ELEMENT FOR ASSAYING FRUCTOSAMINE

[75] Inventor: Hisashi Sakamoto, Kyoto, Japan

[73] Assignee: Kyoto Daiichi Kagaku Co., Ltd., Kyoto, Japan

[21] Appl. No.: 753,371

[22] Filed: Aug. 30, 1991

[30] Foreign Application Priority Data

Aug. 30, 1990 [JP] Japan .................. 2-230912

[51] Int. Cl.$^5$ .......................... C12Q 1/62; G01N 31/22
[52] U.S. Cl. .......................... 435/10; 422/56; 435/805; 435/25; 436/87; 436/170
[58] Field of Search .................. 422/56; 436/87, 170; 435/10, 805, 25

[56] References Cited

U.S. PATENT DOCUMENTS

| | | | |
|---|---|---|---|
| 4,642,295 | 2/1987 | Baker | 436/87 |
| 4,645,742 | 2/1987 | Baker . | |
| 4,956,301 | 9/1990 | Ismail et al. | 436/87 |
| 5,055,388 | 10/1991 | Vogt et al. | 435/10 X |

FOREIGN PATENT DOCUMENTS

| | | |
|---|---|---|
| 0085263 | 8/1983 | European Pat. Off. . |
| 0215170 | 3/1987 | European Pat. Off. . |
| 0250991 | 1/1988 | European Pat. Off. . |
| 0291060 | 11/1988 | European Pat. Off. . |
| 63-182567 | 7/1988 | Japan . |
| 63-15168 | 8/1988 | Japan . |
| 63-304999 | 12/1988 | Japan . |
| 113062 | 3/1989 | Japan . |

OTHER PUBLICATIONS

"Fructosamine: a new approach to the estimation of serum glycosylprotein. An index of diabetic control", Roger N. Johnson, Patricia A. Metcalf and John R. Baker, Clinica Chimica Acta 127; pp. 87–95 (1982).

Primary Examiner—Jill A. Johnston
Attorney, Agent, or Firm—Birch, Stewart, Kolasch & Birch

[57] ABSTRACT

A multilayer analytical element for assaying fructosamine, having a liquid-impermeable support, a buffer-containing layer which contains a buffer having pH of 8 to 12 formed on the support, a tetrazolium salt containing layer which is formed on the buffer-containing layer and, optionally, an intermediate layer interposed between the buffer-containing layer and the tetrazolium salt-containing layer to prevent contact of these two layers, which element assays fructosamine in a short time with good accuracy.

21 Claims, 2 Drawing Sheets

MULTILAYER ANALYTICAL ELEMENT FOR ASSAYING FRUCTOSAMINE

BACKGROUND OF THE INVENTION

1. Field of the Invention

The present invention relates to a multilayer analytical element for assaying fructosamine in a body fluid, in particular, serum.

2. Description of the Related Art

For the measurement of fructosamine in serum, Johnson and Baker proposed a method comprising measuring the reducing power of fructosamine with Nitrotetrazolium Blue (NTB) under alkaline conditions (see Clinica Chimica Acta, 127 (1982) 87–95, Japanese Patent Publication No. 13062/1989, EP-A-085 263 and U.S. Pat. Nos. 4,642,295 and 4,645,742). In this method, the serum is preincubated for 10 minutes to remove the influence of reducing substances in the serum other than fructosamine by reacting such reducing substances with NTB to decompose them, and then NTB consumed in the following 5 minute period (namely from 10 minutes to 15 minutes) is measured since the amount of NTB which is consumed in this 5 minute period is proportional to the amount of fructosamine in the serum.

Japanese Patent Kokai Publication No. 182567/1988 and EP-A-215 170 disclose an end point assay in which interfering substances present in a sample are removed by treating them with a strong base, an oxidizing agent a or an enzyme, or by desalting, the pH of the sample is adjusted to a range between 10 and 14, a color reagent (a tetrazolium salt) is added, and the developed color is measured.

Japanese Patent Kokai Publication No. 15168/1988 and EP-A-250 991 disclose a method comprising pretreating a sample at neutral pH to remove reducing substances and/or turbid materials, adjusting the pH to range between 10 and 12 and adding a color reagent.

Japanese Patent Kokai Publication No. 304999/1988 and EP-A-291 060 disclose a method comprising adding a buffer solution having pH of 9 to 12, a color reagent, uricase and at least one detergent (surfactant) and, after 5 minutes at the earliest, chemically kinetically measuring the change in an absorbance with time in the temperature range between 20° C. and 40° C.

The method of Johnson and Baker is a so-called wet chemistry method and adjusts the temperature at 37° C. under alkaline conditions and then measures the change of absorbance in a time range between 10 minutes and 15 minutes.

The method of Japanese Patent Kokai Publication No. 182567/1988 and EP-A-215 170 is a two-step method, which is troublesome and time-consuming.

In the method of Japanese Patent Kokai Publication No. 304999/1988 and EP-A-291 060, the preincubation requires at least 5 minutes before the reducing substances are removed and turbidity is clarified.

In addition, all the above prior art methods involve wet chemistry and, measure the change of absorbance using a reaction cell.

In general, formazan, which is generated through by reduction of a tetrazolium salt to be used in a color developing reaction with fructosamine, firmly sticks to the reaction cell or the flow cell and increases a background, which is a source of error. When fructosamine is measured with an automatic analyzer which is widely used in many facilities, generated formazan deposits in the reaction tube, a transportation tube, or the flow cell to contaminate the automatic analyzer, so that other components cannot be measured. Since it is difficult to remove deposited formazan, various devices or parts should be immersed in a strong acid or a surfactant overnight.

A reagent for measuring fructosamine is a strong alkaline reagent, for example, having a pH of 10 or greater and its waste liquid is strongly alkaline and pollutes the environment.

In contrast to the wet chemistry method, a so-called dry chemistry method is known. In the dry chemistry method, since one drop (several $\mu l$) of the sample is used for the reaction, the sample is dried when the reaction continues more than 10 minutes and accuracy in measurement deteriorates. When the measuring time is shortened to 10 minutes or less, the measurement is influenced by the reducing substances in the body fluid, so that accurate data are not obtained.

SUMMARY OF THE INVENTION

One object of the present invention is to provide an analytical element for measuring fructosamine in a sample of body fluid by a dry chemistry technique.

Another object of the present invention is to provide an analytical element for easily measuring fructosamine in a sample of body fluid in a short measuring time.

According to the present invention, there is provided a multilayer analytical element for assaying fructosamine comprising a liquid-impermeable support, a buffer-containing layer which contains a buffer having a pH of 8 to 12 formed on said support, a tetrazolium salt-containing layer which is formed on said buffer-containing layer and, optionally, an intermediate layer interposed between said buffer-containing layer and said tetrazolium salt-containing layer to prevent contact of said two layers.

DETAILED DESCRIPTION OF THE INVENTION

Figure 1:
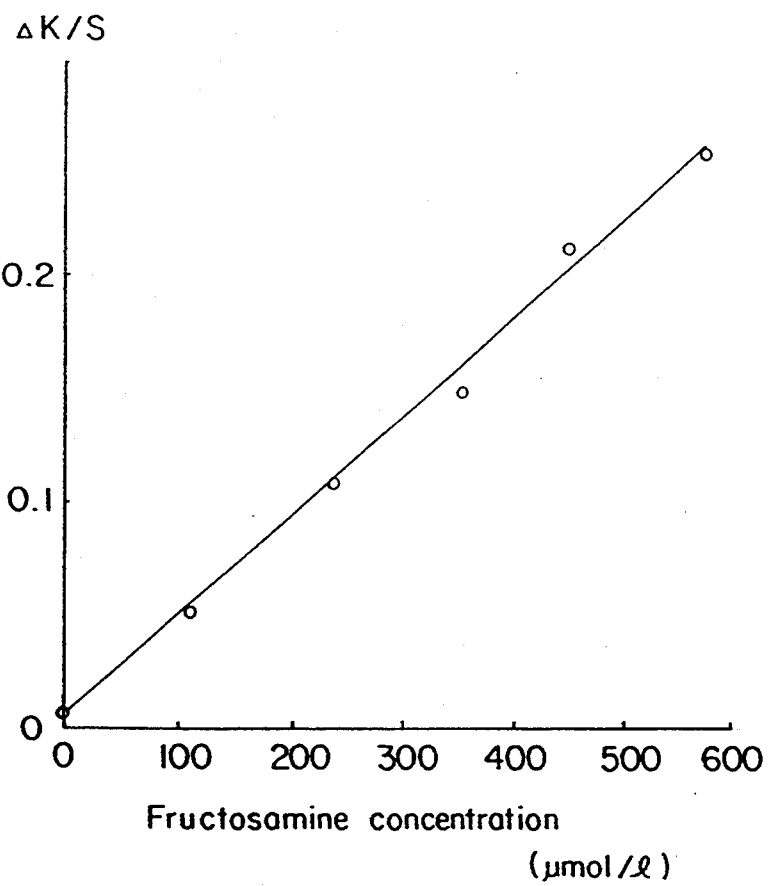
FIG. 1 is a graph showing the relationship between $\Delta K/S$ and fructosamine concentration in a time interval from 5 to 7 minutes in Example 1.

The liquid-impermeable support used in the present invention may be made of any liquid-impermeable material such as a plastic film, paper or a metal foil. Among them, the plastic film is preferred.

The buffer may be any one of conventional buffers having the buffering capacity in a pH range between 8 and 12, preferably between 8.5 and 10.5. In particular, a carbonate buffer is preferred.

The tetrazolium salt to be used in the present invention may be any one of conventional tetrazolium salts that will react with fructosamine to develop a color. Specific examples of the tetrazolium salt are:
3,3'-[3,3'-dimethoxy-(1,1'-biphenyl)-4,4',-diyl]-bis [2-(p-nitrophenyl)-5-phenyl-2H-tetrazolium chloride] (NTB), 3,3'-[3,3'-dimethoxy-(1,1'-biphenyl)-4,4'-diyl]- bis[2,5-bis(p-nitrophenyl)-2H-tetrazolium chloride] (TNTB), 3,3'-(1,1'-biphenyl-4,4'-diyl)-bis(2,5-diphenyl-2H-tetrazolium chloride] (NeoTB), 3-(p-iodophenyl)-2-(p-nitrophenyl)-5-phenyl-2H-tetrazolium chloride (INT), 3-(4,5-dimethyl-2-thiazolyl)-2,5-diphenyl-2H-tetrazolium bromide (MTT), and 2,5-diphenyl-3-(1-naphthyl)-2H-tetrazolium chloride (TV).

The buffer-containing layer of the multilayer analytical element of the present invention may contain uricase. Since uricase decomposes uric acid, which is one of the reducing substances in the body liquid, in a short time, it will suppress the influence of uric acid during the assay of fructosamine and shorten the assay time.

The multilayer analytical element of the present invention can be prepared by successively laminating the buffer-containing layer, the optional intermediate layer and the tetrazolium salt-containing layer on the liquid-impermeable support.

For example, the alkaline buffer-containing layer is formed on the support by dissolving the buffer and a binder in the suitable solvent, applying a resulting solution on the support, and drying it. Preferably, the binder is a hydrophilic polymer such as polyvinylpyrrolidone (PVP), hydroxypropylcellulose (HPC), methylcellulose (MC), polyacrylamide, gelatin, etc. When a hydrophilic polymer is used, the solvent is an aqueous solvent, in particular, water.

When an intermediate layer is provided, it is formed by dissolving a binder resin in a solvent in which neither the buffer nor the tetrazolium salt is dissolved, applying the resulting solution on the formed buffer-containing layer and drying it to form a binder resin film. As the solvent, isopropanol, acetone, chloroform, methyl chloride and toluene are preferred. As the binder resin, HPC, PVP and the like are used.

The tetrazolium salt-containing layer is formed by impregnating a solution of the salt in a porous matrix such as a filter paper, woven or knit fabric or a membrane filter and drying it. Then, the porous matrix containing the impregnated tetrazolium salt is laminated on the buffer-containing layer or the intermediate layer. Solvents in which a specific tetrazolium salt is dissolved are well known. To improve the solubility of the tetrazolium salt in the solvent, a surfactant may be added to the solvent.

The thickness of each of the buffer-containing layer, the intermediate layer and the tetrazolium salt-containing layer is not critical. Preferably, the buffer-containing layer has a wet thickness of 250 $\mu$m or less, e.g. about 200 $\mu$m, the intermediate layer has a wet thickness of 200 $\mu$m or less, e.g., about 150 $\mu$m, and the tetrazolium salt-containing layer has a thickness of 300 $\mu$m or less, e.g., about 250 $\mu$m.

The laminate of the buffer-containing layer, the optional intermediate layer and the tetrazolium salt-containing layer is cut to a suitable size, for example, 5 mm×7 mm, fixed to a base film with a double coated tape or an adhesive and used in the assay.

The assay of fructosamine is carried out by placing a drop of a sample on the multilayer analytical element of the present invention and measuring the developed color by a conventional method. A specific assay manner will be explained in below described Examples.

PREFERRED EMBODIMENTS OF THE INVENTION

The present invention will be illustrated by following Examples.

Example 1

A buffer-containing layer was formed by mixing the following components, applying the resulting mixture on an opaque polyethylene terephthalate film at a wet thickness of 200 $\mu$m and drying it at 40° C. for 30 minutes:

| | |
|---|---|
| Sodium carbonate | 3.18 g |
| Sodium hydrogencarbonate | 0.84 g |
| Purified water | 86 g |
| PVP K-90 | 10 g |

A tetrazolium salt-containing layer was formed by mixing the following components, impregnating a cotton or polyester fabric with the resulting mixture and drying it at 40° C. for 30minutes:

| | |
|---|---|
| NTB | 700 mg |
| Methanol | 10 g |
| Purified water | 14.3 g |

A mixture of HPC (2 g) and isopropanol (98 g) was coated as an intermediate layer on the buffer-containing layer and then the tetrazolium salt-containing layer was laminated thereon and dried at 40° C. for 30 minutes.

The produced laminated was cut to a size of 5 mm×7 mm and fixed at one end of a polyethylene terephthalate strip (5 mm×80 mm) with a double coated tape to obtain a sample element.

Linearity

Human serum containing fructosamine at a high concentration was stepwise diluted with purified water. Each 6 $\mu$l of the diluted serum was spotted on the sample element and incubated at 37° C. Then, the reflectance from 5 to 7 minutes from the start of incubation was monitored. The measured reflectance was converted to a K/S value according to the Kubelka-Munk equation, and its difference ($\Delta$K/S) was calculated. The results are shown in Table 1.

TABLE 1

| Concentration of fructosamine ($\mu$mol/l) | $\Delta$K/S between 5 and 7 minutes |
|---|---|
| 0 | 0.006 |
| 116 | 0.048 |
| 232 | 0.106 |
| 348 | 0.150 |
| 464 | 0.211 |
| 580 | 0.252 |

These data are plotted in FIG. 1 and show good dilution linearity.

Example 2

Influence of co-existing materials in body fluid (1) Influence of ascorbic acid

To human serum, ascorbic acid was added to prepare test samples having various concentrations of ascorbic acid. Then, each 6 $\mu$l of the test sample was spotted on the sample element which was produced in the same manner as in Example 1 and incubated at 37° C. $\Delta$K/S was calculated in the same manner as in Example 1. The results are shown in Table 2.

TABLE 2

| Concentration of ascorbic acid (mg/dl) | ΔK/S between 5 and 7 minutes |
| --- | --- |
| 0 | 0.135 |
| 10 | 0.137 |
| 20 | 0.133 |
| 30 | 0.138 |
| 40 | 0.134 |

As seen from the results of Table 2, the multi-layer analytical element of the present invention is hardly influenced by ascorbic acid.

(2) Influence of uric acid

To human serum, uric acid was added to prepare test samples having various concentrations of uric acid. Then, each 6 μl of the test sample was spotted on the sample element which was produced in the same manner as in Example 1 and incubated at 37° C. ΔK/S was calculated in the same manner as in Example 1. The results are shown in Table 3.

TABLE 3

| Concentration of uric acid (mg/dl) | ΔK/S between 5 and 7 minutes |
| --- | --- |
| 5.2 | 0.128 |
| 12.2 | 0.132 |
| 19.6 | 0.140 |
| 25.8 | 0.129 |
| 34.0 | 0.132 |

Though the ΔK/S tends to be slightly increased due to the presence of uric acid, the multilayer analytical element of the present invention is not substantially influenced by uric acid.

Figure 2:
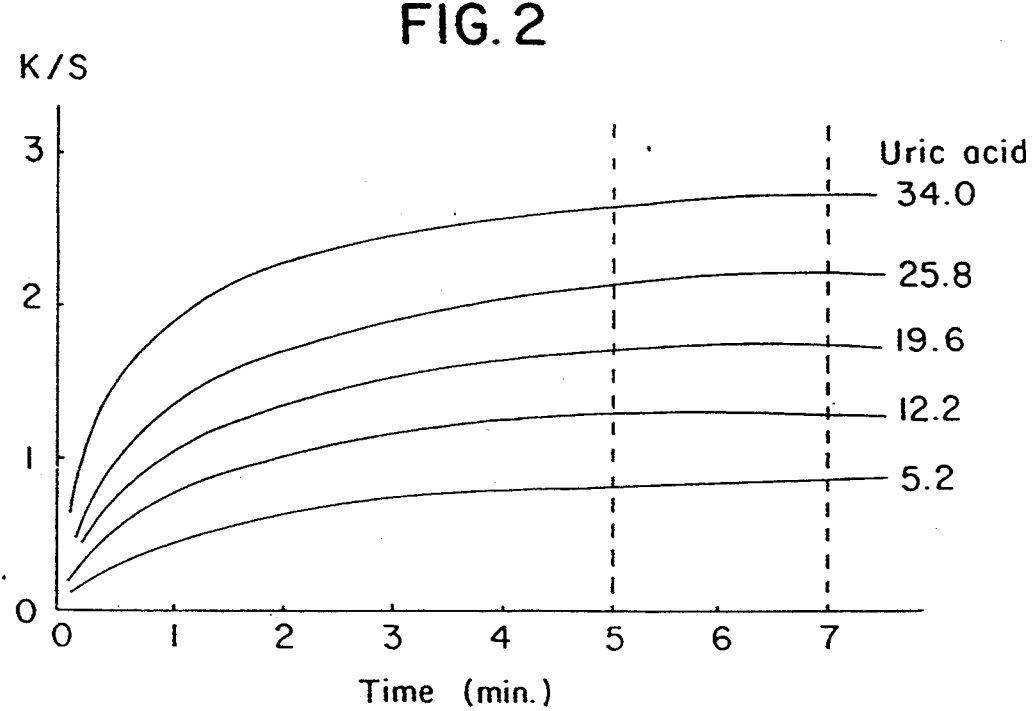
FIG. 2 is a graph showing the change of K/S with time in Example 2.

From the change of ΔK/S with time shown in FIG. 2, it is understood that substantially all uric acid reacts with NTB within 5 minutes.

The multilayer analytical element of the present invention is hardly influenced by glutathione, bilirubin or hemolysis turbidity.

Example 3

Figure 3:
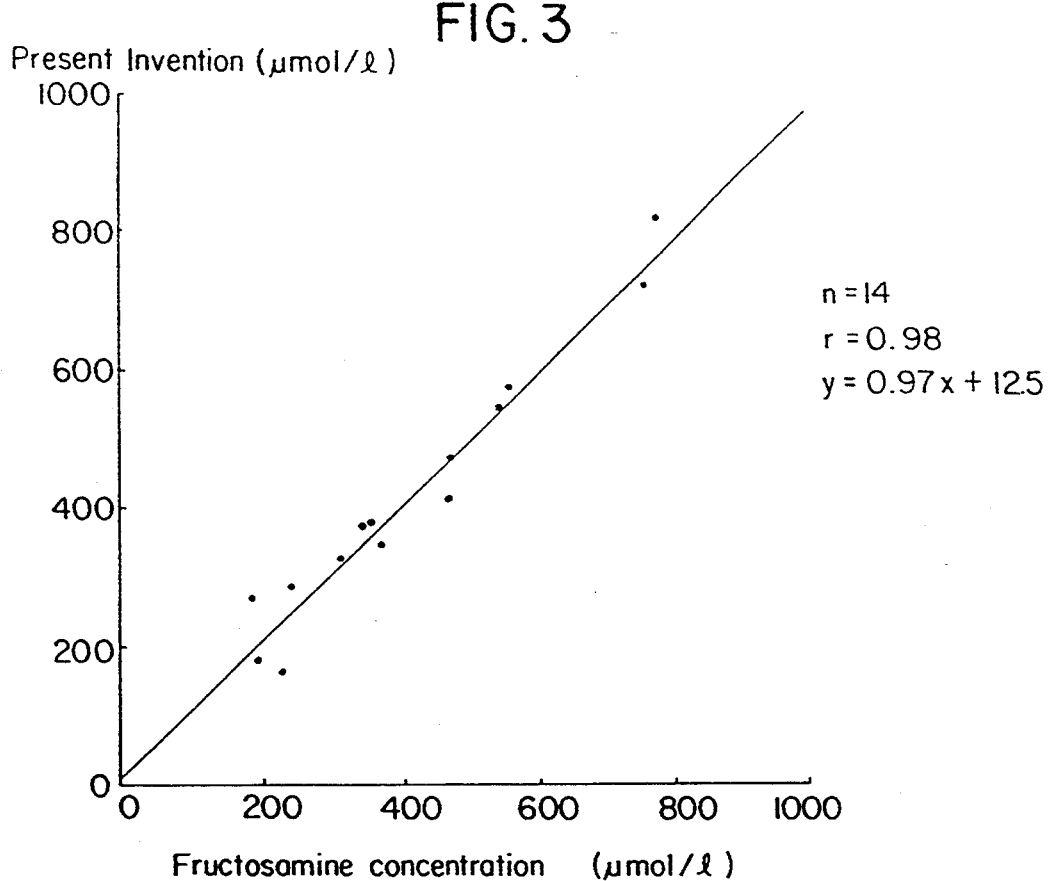
FIG. 3 is a graph showing the correlation between measurement according to the present invention and the conventional method.

Using various human sera, correlation with the Reference method (using the Roche kit) was checked. As seen from FIG. 3, the correlation coefficient r was 0.98 and the multilayer analytical element of the present invention shows good correlation with the Reference method.

Example 4

A buffer-containing layer was formed by mixing the following components, applying the resulting mixture on an opaque polyethylene terephthalate film at a wet thickness of 200 μm and drying it at 40° C. for 30 minutes:

| Sodium carbonate | 0.318 g |
| --- | --- |
| Sodium hydrogencarbonate | 0.084 g |
| Purified water | 8.6 g |
| PVP K-90 | 1.0 g |
| Uricase | 4000 Units |

A tetrazolium salt-containing layer was formed by mixing the following components, impregnating polyester fabric with the resulting mixture and drying it at 40° C. for 30 minutes:

| NTB | 700 mg |
| --- | --- |
| Methanol | 10 g |
| Purified water | 14.3 g |

A mixture of HPC (2 g) and isopropanol (98 g) was coated as an intermediate layer on the buffer-containing layer and then the tetrazolium salt-containing layer was laminated thereon and dried at 40° C. for 30 minutes.

The produced laminated was cut to a size of 5 mm×7 mm and fixed at one end of a polyethylene terephthalate strip (5 mm×80 mm) with a double coated tape to obtain a sample element.

Figure 4:
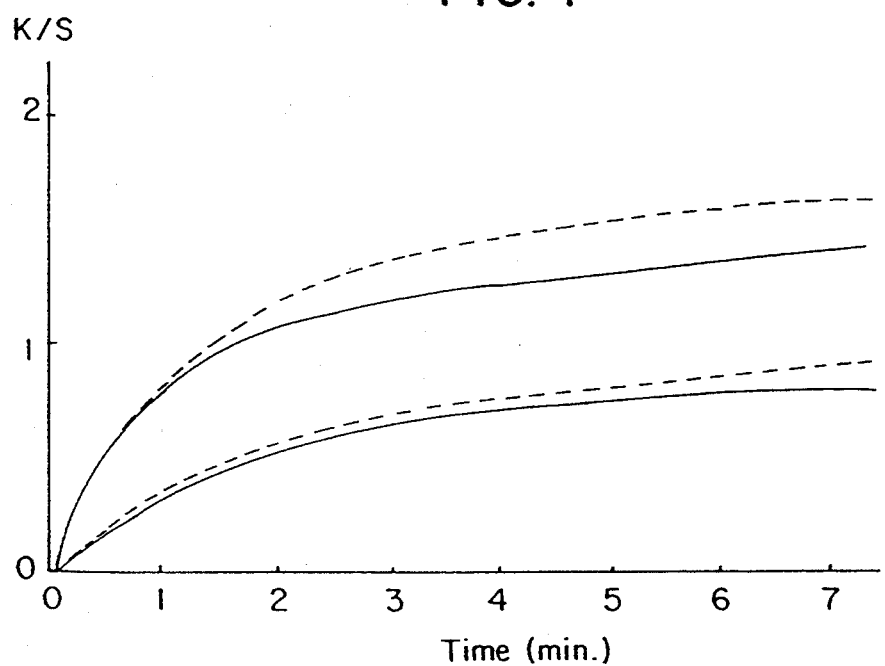
FIG. 4 is a graph showing the change of K/S with time for the sample elements of Example 1 (broken lines) and Example 4 (solid lines).

Each 6 μl of a human serum and a human serum containing about 20 mg/dl of uric acid was spotted on each of the analytical elements produced in Examples 1 and 4, and ΔK/S was calculated in the same manner as in Example 1, except for the measuring time period. The results are shown in Table 4 and FIG. 4.

TABLE 4

| | Example 4 | | Example 1 | |
| --- | --- | --- | --- | --- |
| | ΔK/S between 4 and 6 min. | ΔK/S between 5 and 7 min. | ΔK/S between 4 and 6 min. | ΔK/S between 5 and 7 min. |
| Serum | 0.148 | 0.147 | 0.158 | 0.149 |
| Serum + Uric acid | 0.150 | 0.148 | 0.169 | 0.152 |

In Example 4, when the assay time is shifted to the range between 4 minutes and 6 minutes, fructosamine can be assayed without suffering from the influence of uric acid.

What is claimed is:

1. A multilayer analytical element for assaying fructosamine, comprising a liquid-impermeable support, a buffer-containing layer which contains a buffer having a pH of 8 to 12 formed on said support, wherein said buffer-containing layer contains uricase, a tetrazolium salt-containing layer which is formed on said buffer-containing layer, and an intermediate layer interposed between said buffer-containing layer and said tetrazolium salt-containing layer to prevent contact of said buffer-containing layer and said tetrazolium salt-containing layer.

2. The multilayer analytical element according to claim 1, wherein said tetrazolium salt contained in said tetrazolium salt-containing layer is at least one selected from the group consisting of 3,3'-[3,3'-dimethoxy- (1,1'-biphenyl)-4,4'-diyl ]-bis[2-(p-nitrophenyl)-5-phenyl-2H-tetrazolium chloride], 3,3'-[3,3'-dimethoxy-(1,1'-biphenyl)-4,4'-diyl]-bis[2,5-bis(p-nitrophenyl)-2H-tetrazolium chloride], 3,3'-(1,1'-biphenyl-4,4'-diyl)-bis(2,5-diphenyl-2H-tetrazolium chloride], 3-(p-iodophenyl)-2-(p-nitrophenyl)-5-phenyl-2H-tetrazolium chloride, 3-(4,5-dimethyl-2- thiazolyl)-2,5-diphenyl-2H-tetrazolium bromide and 2,5-diphenyl-3-(1-naphthyl)-2H-tetrazolium chloride.

3. The multilayer analytical element according to claim 1, wherein said buffer has a pH of 8.5 to 10.5.

4. The multilayer analytical element according to claim 1, wherein said liquid-impermeable support is a material selected from the group consisting of a plastic film, paper, and a metal foil.

5. The multilayer analytical element according to claim 1, wherein said liquid-impermeable support is a plastic film.

6. The multilayer analytical element according to claim 1, wherein said buffer is a carbonate buffer.

7. The multilayer analytical element according to claim 1, wherein said buffer-containing layer further comprises a binder.

8. The multilayer analytical element according to claim 7, wherein said binder is a hydrophilic polymer.

9. The multilayer analytical element according to claim 8, wherein said hydrophilic polymer is a member selected from the group consisting of polyvinylpyrrolidone, hydroxypropylcellulose, methylcellulose, polyacrylamide, and gelatin.

10. The multilayer analytical element according to claim 1, wherein said intermediate layer comprises a binder resin.

11. The multilayer analytical element according to claim 10, wherein said binder resin is hydroxypropylcellulose or polyvinylpyrrolidone.

12. The multilayer analytical element according to claim 1, wherein said tetrazolium salt-containing layer is formed by impregnating a solution of said salt in a porous matrix.

13. The multilayer analytical element according to claim 12, wherein said porous matrix is a member selected from the group consisting of a filter paper, a woven fabric, a knit fabric, and a membrane filter.

14. The multilayer analytical element according to claim 1, wherein said buffer-containing layer has a wet thickness of 250 μm or less and said tetrazolium salt-containing layer has a thickness of 300 μm or less.

15. The multilayer analytical element according to claim 14, wherein said buffer-containing layer has a wet thickness of about 200 μm and said tetrazolium salt-containing layer has a thickness of about 250 μm.

16. The multilayer analytical element according to claim 1, wherein said intermediate layer has a wet thickness of 200 μm or less.

17. The multilayer analytical element according to claim 16, wherein said intermediate layer has a wet thickness of about 150 μm.

18. The multilayer analytical element according to claim 1, wherein said liquid-impermeable support is an opaque polyethylene terephthalate film, said buffer-containing layer is formed by mixing sodium carbonate, sodium hydrogencarbonate, water, and a polyvinylpyrrolidone polymer, said tetrazolium salt-containing layer is a cotton or polyester fabric impregnated with a mixture formed by mixing 3,3'-[3,3'-dimethoxy-(1,1'-biphenyl)-4,4'-diyl]-bis[2-(p-nitrophenyl)-5-phenyl2-H-tetrazolium chloride], methanol, and water, and said intermediate layer is formed by mixing hydroxypropylcellulose and isopropanol.

19. The multilayer analytical element according to claim 1, wherein said liquid-impermeable support is an opaque polyethylene terephthalate film, said buffer-containing layer is formed by mixing sodium carbonate, sodium hydrogencarbonate, water, a polyvinylpyrrolidone polymer, and uricase, said tetrazolium salt-containing layer is a polyester fabric impregnated with a mixture formed by mixing 3,3'-[3,3'-dimethoxy-(1,1'-biphenyl)-4,4'-diyl]-bis[2-(p-nitrophenyl)-5-phenyl-2H-tetrazolium chloride], methanol, and water, and said intermediate layer is formed by mixing hydroxypropylcellulose and isopropanol.

20. A method for assaying fructosamine, comprising the steps of:
   (a) placing a sample of body fluid on said multilayer analytical element of claim 2;
   (b) measuring the amount of color developed; and
   (c) determining the amount of fructosamine by comparing the amount of color developed to values on a standard curve.

21. The method according to claim 20, wherein said measuring is conducted by monitoring the reflectance from said sample of body fluid.

* * * * *